United States Patent
Conrath

Patent Number: 5,478,829
Date of Patent: Dec. 26, 1995

[54] SOLUTION OF SPARFLOXACIN, ITS PREPARATION AND SALT OF WHICH IT IS COMPOSED

[75] Inventor: Guillaume Conrath, Châtenay-Malabry, France

[73] Assignee: Rhone-DPC Europe, Antony, France

[21] Appl. No.: 211,057

[22] PCT Filed: Sep. 25, 1992

[86] PCT No.: PCT/FR92/00891

§ 371 Date: Mar. 25, 1994

§ 102(e) Date: Mar. 25, 1994

[87] PCT Pub. No.: WO93/05782

PCT Pub. Date: Apr. 1, 1993

[30] Foreign Application Priority Data

Sep. 27, 1991 [FR] France .................... 91 11913

[51] Int. Cl.$^6$ .................... A61K 31/495; A61K 31/47; C07D 401/04
[52] U.S. Cl. .................... 514/254; 544/363
[58] Field of Search .................... 544/363; 514/254

[56] References Cited

U.S. PATENT DOCUMENTS 4,795,751  1/1989  Matsumoto et al. .................... 514/254

FOREIGN PATENT DOCUMENTS 0221463  5/1987  European Pat. Off. .

*Primary Examiner*—Raymond Henley, III
*Assistant Examiner*—Phyllis G. Spivack
*Attorney, Agent, or Firm*—Finnegan, Henderson, Farabow, Garrett & Dunner

[57] ABSTRACT

This invention relates to a pharmaceutical composition comprising sparfloxacin and a stable aqueous solution of sparfloxacin of the formula (I):

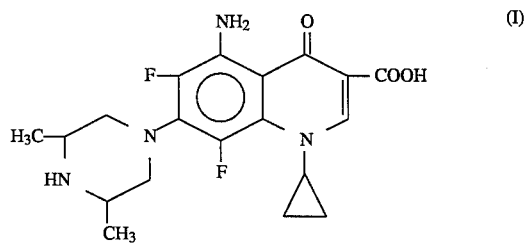

comprising sparfloxacin, one or more polyhydroxymonocarboxylic acids, or lactone derivatives thereof, at least in a stoichiometric quantity with respect to sparfloxacin, and, optionally, an excess of said polyhydroxymonocarboxylic acid or another pharmaceutically acceptable acid for ensuring full solubilization of the salt so formed, not exceeding 5, and optionally an isotonic agent and/or other pharmaceutically acceptable additives.

10 Claims, No Drawings

SOLUTION OF SPARFLOXACIN, ITS PREPARATION AND SALT OF WHICH IT IS COMPOSED

This application is a 371 of PCT/FR92/00841, filed Sep. 25, 1992.

FIELD OF THE INVENTION

The present invention relates to a novel pharmaceutical composition suitable for the parenteral administration of sparfloxacin.

BACKGROUND OF THE INVENTION

Sparfloxacin of formula:

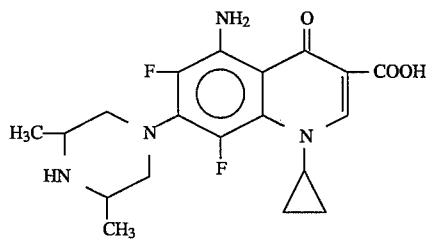

as well as its addition salts with acids or bases, useful as antimicrobial agents, have been described in Patent Application EP 221,463.

Patent Application EP 284935 also describes quinolones and their salts and, amongst these products, sparfloxacin.

Unfortunately, the salts of sparfloxacin are generally insoluble or unstable in solution. It has thus not been possible until now to prepare suitable compositions for parenteral administration.

European Patent EP 322,892 mentions these difficulties and describes lyophilised compositions containing a salt of sparfloxacin with an acid. However, these compositions do not allow stable solutions to be obtained for a prolonged period and for this reason only the preparation of a solution to be used at once is possible. In addition, such solutions risk being unsuitable for use in slow perfusions.

DESCRIPTION OF THE INVENTION

The present invention relates to stable injectable solutions. These compositions can be kept for a prolonged period and are in general stable to heat.

The solutions according to the invention are aqueous solutions containing:

sparfloxacin one or more polyhydroxymonocarboxylic acids or their lactone derivatives, at least in a stoichiometric quantity with respect to sparfloxacin, if necessary an excess of the polyhydroxymonocarboxylic acid or another pharmaceutically acceptable acid intended to ensure a pH of complete solubilization of the salt thus formed, of less than or equal to 5, if appropriate, a tonicity regulator and/or other pharmaceutically acceptable adjuvants.

The solutions according to the invention contain at least 1% of sparfloxacin. However, they can contain concentrations which can increase to 40% of sparfloxacin. It is well known that solutions of concentration less than 1% are likewise practicable and clinically utilisable; these solutions likewise come within the scope of the present invention.

The polyhydroxymonocarboxylic acid is chosen in such a way that its $pK_a$ is greater than 3 at 25° C. By way of example, it can be chosen from amongst lactobionic, glucoheptonic, gluconic or ascorbic acid.

The quantity of the polyhydroxymonocarboxylic acid is a function of the quantity of sparfloxacin. It is determined so as to have at least stoichiometric proportions and in such a way as preferably to obtain solutions in which the pH is not less than 3.5.

The acid capable of ensuring complete solubilization can be chosen from amongst the pharmaceutically acceptable acids which do not risk, by reason of their nature and/or their concentration, displacing, in a significant fashion, the salt of sparfloxacin with the polyhydroxymonocarboxylic acid. By way of example, organic acids can be chosen such as acetic acid, propionic acid, tartaric acid, succinic acid or hydroxy- or polyhydroxymonocarboxylic acids. Stronger acids can likewise be utilized, particularly such as sulphonic acids (methanesulphonic acid for example), carboxylic acids (maleic acid, oxalic acid, malonic acid for example), or mineral acids (for example hydrochloric acid, phosphoric acid, sulphuric acid) in the cases where their concentration can be fixed in such a way that they do not risk displacing, in a significant fashion, the salt of sparfloxacin with the polyhydroxymonocarboxylic acid. However, it is understood that for reasons of convenience, it is quite advantageous to adjust the solubility and the pH of the solutions by means of the polyhydroxymonocarboxylic acid employed.

The pH of the solutions is less than or equal to 5. In a general manner, the pH of the solutions may be compatible with direct administration. It is preferably between 3.5 and 5.

Preferably, the solutions according to the invention are isotonic. However, non-isotonic solutions intended for injection in a glucose perfusion bag likewise come within the scope of the present invention.

The solutions according to the invention can be rendered isotonic by addition of a tonicity regulator such as, for example, glucose, glycerol, sorbitol, mannitol, xylitol, fructose or lactose.

The solutions according to the invention are more especially intended for administration by the parenteral route. They can likewise be utilized by the oral, ocular or auricular route or in local administration to the skin and the mucous membranes.

It is understood that the solutions according to the invention can contain, besides the tonicity regulator, other compatible and pharmaceutically acceptable adjuvants. By way of example, they can likewise contain sweeteners, flavorings, preservatives, colorants or, if appropriate, gelling agents.

It is understood that the salts of sparfloxacin with the hydroxy- or polyhydroxymonocarboxylic acid thus obtained, which allow the preparation and the use of stable injectable solutions, also come within the scope of the present invention.

The solutions according to the invention are alternatively prepared by addition of water to a mixture comprising sparfloxacin, the polyhydroxymonocarboxylic acid(s) chosen, in an at least stoichiometric quantity with respect to sparfloxacin, if necessary the excess of the polyhydroxymonocarboxylic acid or the other acid intended to ensure a pH of solubilization of the salt of sparfloxacin of less than or equal to 5 and/or the tonicity regulator and the other adjuvants, or else by addition of sparfloxacin and if appropriate other additives to a solution of the polyhydroxymonocarboxylic acid(s).

The preparation and the division of the solution are preferably carried out under nitrogen. The solutions thus obtained can be sterilized by heat (sterilization in an autoclave). In the case of solutions of the ascorbic acid salt, however, it is preferable to work with sterilizing filtration.

It is likewise possible to prepare the solutions according to the invention by means of lactone derivatives which, by hydrolysis, generate the hydroxy- or polyhydroxymonocarboxylic acids in situ.

The solutions according to the invention have the advantage of very good physicochemical stability.

They are particularly of interest insofar as they give access to liquid formulations of sparfloxacin which until now have not been practicable, particularly to an injectable formulation, stable to light under the normal conditions of use and stable to heat while having a pH compatible with direct administration. This novel formulation is particularly advantageous for storage, convenience and rapidity of utilization of a form ready-to-use and also in the case of slow perfusions. In addition, and taking account of the good solubility of the salts obtained under the pH conditions used, these solutions can if necessary be concentrated, which allows a varied choice of doses to be formulated.

EXAMPLES

The following examples, given in a non-limiting capacity, illustrate the present invention.

Example 1

Preparation of a solution containing sparfloxacin (4 mg/ml), rendered isotonic with glucose.

Sparfloxacin (400 mg) is mixed with δ-gluconolactone (321 mg) and glucose monohydrate (4.75 g). This powder mixture is dissolved in water for injection previously rendered inert with nitrogen. Dissolution is achieved by stirring under nitrogen. The volume is made up to 100 ml with water for injections. The solution thus obtained is sterilized in an autoclave (120° C., 20 minutes).

The pH of the solution is 3.8.

This solution remains clear after keeping for 5 months at 4°, 20° and 35° C., without modifying the pH.

Example 2

Preparation of a solution containing sparfloxacin (10 mg/ml) rendered isotonic with glucose.

Working as above in Example 1, but adjusting the volume to 40 ml and employing glucose (1.74 g) monohydrate, a clear solution is obtained in which the pH is 3.8.

Such a solution prepared on a 2.5-liter scale remains clear and is not modified in pH over a period of at least 5 months and under the following temperature conditions: 20° C., 4° C. and 35° C.

An HPLC analysis carried out after keeping for 3 months at 20° C., 4° C., 35° C. and 45° C. did not show any degradation of the product.

Example 3

Preparation of a solution containing sparfloxacin (20 mg/ml) rendered isotonic with glucose.

Working as previously in Example 1 but adjusting the volume to 20 ml and by addition of glucose monohydrate (770 mg), a clear solution is prepared in which the pH is 3.7.

This solution prepared on a 2-liter scale remains clear and is not modified in pH after keeping for 3 months at 20°, 4°, 35° and 45° C.

The HPLC analysis carried out after 1 month of keeping at 20°, 35° and 45° C. does not reveal any degradation product.

Example 4

Preparation of a solution containing sparfloxacin (50 mg/ml) rendered isotonic with glucose.

Working as in Example 1, but adjusting the volume to 8 ml and by addition of glucose (130 mg) monohydrate, a clear solution is prepared in which the pH is 3.5.

This solution prepared on a 2-liter scale remains clear and is not modified in pH after keeping for 3 months at 20°, 4°, 35° and 45° C.

The HPLC analysis carried out after keeping for 1 month at 20°, 35° and 45° C. does not reveal any degradation product.

Example 5

Preparation of a solution containing hypertonic sparfloxacin (100 mg/ml).

Working as in Example 1, but adjusting the volume to 4 ml and without addition of glucose, a solution is prepared in which the pH is 3.5.

This solution prepared on a 1-liter scale remains clear and is not modified in pH after keeping for 3 months at 20°, 4°, 35° and 45° C.

The HPLC analysis carried out after keeping for 1 month at 20°, 35° and 45° C. does not reveal any degradation product.

Example 6

Preparation of a solution containing hypertonic sparfloxacin (200 mg/ml).

Working as in Example 1, but adjusting the volume to 2 ml and without adding glucose, a clear solution is prepared in which the pH is 3.5.

This solution prepared on a 1-liter scale remains clear and is not modified in pH after keeping for 3 months at 20°, 4°, 35° and 45° C.

The HPLC analysis carried out after keeping for 1 month at 20°, 35° and 45° C. does not reveal any degradation product.

Example 7

Preparation of a solution containing sparfloxacin (10 mg/ml).

Sparfloxacin (1,000 mg) is mixed with lactobionic acid (1.79 g). This powder mixture is dissolved in water for injections previously rendered inert with nitrogen. Dissolution is achieved by stirring under nitrogen. The volume is made up to 100 ml with water for injections. The solution thus obtained is sterilized in an autoclave (120° C., 20 minutes).

The pH of the solution is 3.75.

This solution kept for 5 months at 4° and at 20° C. remains clear and without modification of pH.

An HPLC determination after keeping for 5 months does not show any degradation impurities.

Example 8

Preparation of a solution containing sparfloxacin (20 mg/ml).

Working as in Example 7, but starting from sparfloxacin (2,000 mg) and lactobionic acid (3.58 g) and adjusting the volume to 100 ml, a clear solution of pH=3.5 is obtained.

Example 9

Preparation of a solution containing sparfloxacin (30 mg/ml).

Working as in Example 7, but starting from sparfloxacin (3,000 mg) and lactobionic acid (8.96 g) and adjusting the volume to 100 ml, a clear solution of pH=3.5 is obtained.

Example 10

Preparation of a solution containing sparfloxacin (10 mg/ml).

Working as in Example 7, but starting from sparfloxacin (1,000 mg) and glucoheptonic acid (2.26 g) and adjusting the volume to 100 ml, and after heating to 50° C. for 1 hour, a clear solution of pH=4.3 is obtained.

Example 11

Preparation of a solution containing sparfloxacin (10 mg/ml) rendered isotonic with glucose.

Sparfloxacin (1,000 mg) is mixed with ascorbic acid (528 mg) and anhydrous glucose (4 g). This powder mixture is dissolved in water for injections previously rendered inert with nitrogen. The dissolution is carried out by stirring under nitrogen. The volume is made up to 100 ml with water for injections. The solution thus obtained is sterilized by sterilising filtration.

The pH of the solution is 4.8.

This solution kept 7 months at 4° and at 20° C., protected from light, remains clear and without modification of pH.

An HPLC determination after keeping for 7 months does not show any degradation impurities.

Example 12

Preparation of a solution containing sparfloxacin (10 mg/ml), rendered isotonic with glycerol.

Working as in Example 11, but starting from glycerol (2.2 g) in place of the glucose, a clear solution of pH=5 is obtained.

This solution remains clear after 7 months at 4° and 20° C., protected from light and without modification of pH.

An HPLC determination after keeping for 7 months does not show any degradation impurities.

Example 13

Preparation of a solution containing sparfloxacin (20 mg/ml).

Working as in Example 11, but starting from sparfloxacin (2,000 mg) and from ascorbic acid (1.76 g), a clear solution of pH=4.2 is obtained.

This solution remains clear after 7 months at 20° C., protected from light.

I claim:

1. A stable aqueous solution of sparfloxacin of formula:

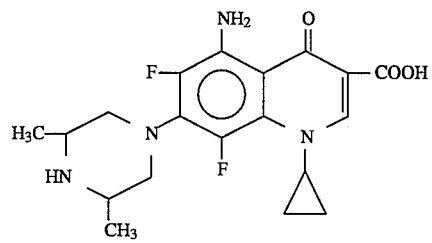

which comprises:

sparfloxacin at least one polyhydroxymonocarboxylic acid or its lactone derivative, at least in a stoichiometric quantity with respect to sparfloxacin, optionally an excess of the polyhydroxymonocarboxylic acid or another pharmaceutically acceptable acid intended to ensure a pH of complete solubilization of the salt thus formed, of less than or equal to 5, optionally, a tonicity regulator and/or other pharmaceutically acceptable adjuvant.

2. A solution according to claim 1, wherein the polyhydroxymonocarboxylic acid is selected from the acids having a $pK_A$ greater than 3 at 25° C.

3. A solution according to claim 1, wherein the polyhydroxymonocarboxylic acid is selected from:

lactobionic acid, glucoheptonic acid, gluconic acid and ascorbic acid.

4. A solution according to claim 1, wherein the concentration of sparfloxacin is up to about 40%.

5. A solution according to claim 1, wherein pH is between 3.5 and 5.

6. A solution according to claim 1, wherein the tonicity regulator is selected from glucose, glycerol, sorbitol, mannitol, xylitol, fructose and lactose.

7. Method for preparation of a solution according to claim 1, comprising adding water to a mixture of sparfloxacin, at least one polyhydroxymonocarboxylic acid in an at least stoichiometric quantity with respect to sparfloxacin and, optionally, an excess of the polyhydroxymonocarboxylic acid or another acid capable of ensuring a pH of complete solubilization of the salt of less than or equal to 5 and/or a tonicity regulator and other adjuvant.

8. Method for preparation of a solution according to claim 1, comprising adding the sparfloxacin, optionally, an acid able to ensure a complete solubilization pH of the salt of less than or equal to 5 and/or a tonicity regulator and other adjuvants to a solution of at least one polyhydroxymonocarboxylic acid.

9. A salt of sparfloxacin with a polyhydroxymonocarboxylic acid selected from:
  lactobionic acid,
  glucoheptonic acid and
  ascorbic acid.

10. A pharmaceutical composition comprising an effective amount of a solution according to claim 1, optionally in association with at least one compatible and pharmaceutically acceptable diluent or adjuvant.

\* \* \* \* \*